United States Patent
Knauf et al.

(10) Patent No.: US 9,815,769 B2
(45) Date of Patent: Nov. 14, 2017

(54) PROCESS FOR THE PREPARATION OF DI- AND POLYAMINES FROM THE DIPHENYLMETHANE SERIES

(71) Applicant: Covestro Deutschland AG, Monheim am Rhein (DE)

(72) Inventors: Thomas Knauf, Dormagen (DE); Stefan Wershofen, Monchengladbach (DE); Klaus-Gerd Gruner, Duisburg (DE); Esteve Obis Torruella, CP Tarragona (ES)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/785,498

(22) PCT Filed: Apr. 22, 2014

(86) PCT No.: PCT/EP2014/058044
§ 371 (c)(1),
(2) Date: Oct. 19, 2015

(87) PCT Pub. No.: WO2014/173856
PCT Pub. Date: Oct. 30, 2014

(65) Prior Publication Data
US 2016/0068474 A1 Mar. 10, 2016

(30) Foreign Application Priority Data
Apr. 24, 2013 (EP) ..................... 13165198

(51) Int. Cl.
*C07C 209/78* (2006.01)
*C07C 263/10* (2006.01)
*C08G 73/02* (2006.01)

(52) U.S. Cl.
CPC .......... *C07C 209/78* (2013.01); *C07C 263/10* (2013.01); *C08G 73/0266* (2013.01)

(58) Field of Classification Search
CPC .................................................. C07C 209/78
See application file for complete search history.

(56) References Cited

U.S. PATENT DOCUMENTS

| | | |
|---|---|---|
| 3,676,497 A | 4/1972 | Recchia et al. |
| 5,053,539 A | 10/1991 | Yano et al. |
| 5,286,760 A | 2/1994 | Bolten et al. |
| 6,433,219 B1 | 8/2002 | Stroefer et al. |
| 6,576,788 B1 | 6/2003 | Penzel et al. |
| 6,649,798 B2 | 11/2003 | Klein et al. |
| 6,831,192 B2 | 12/2004 | Stroefer et al. |
| 7,186,857 B2 | 3/2007 | Muller et al. |
| 7,253,321 B2 | 8/2007 | Hagan et al. |
| 7,528,283 B2 | 5/2009 | Pohl et al. |
| 2009/0240077 A1 | 9/2009 | Wershofen et al. |
| 2012/0035396 A1* | 2/2012 | Stroefer ............... C07C 209/62 564/333 |

FOREIGN PATENT DOCUMENTS

| | | |
|---|---|---|
| DE | 844896 | 9/1952 |
| GB | 1517585 | 7/1978 |

OTHER PUBLICATIONS

Gould, David, F., "Phenolic Resins", 1959, Reinhold Publishing Corporation, New York, New York, United States, p. 34, XP002710765.
Rompp—quotation "aliphatische Verbindungen" [Aliphatic compounds]—Georg Thieme; p. 1; Last update Jul. 2009; English language translation attached.
Ullmann's Encyclopedia of Technical Chemistry; "Mineral oil and natural gas to formazan dyes"; pp. 695-696; 4th newly revised and extended edition; vol. 11; Verlag Chemie, Weinheim/Bergstr.; 1976; English language translation attached.
Office Action dated Nov. 25, 2016 in EP Application No. 14 720 072.9-1302; English language translation attached.
Ullmanns Encyklopädie der technischen Chemie; 4., neubearbeitete und erweiterte Auflage; Band 11; pp. 695-696 (formaldehyde); Erdöl und Erdgas bis Formazanfarbstoffe; 1976; Verlag Chemie, Weinheim/Bergstr.
Römpp, quotation "aliphatische Verbindungen" (aliphatic compounds), Jul. 2009.

* cited by examiner

*Primary Examiner* — Shawquia Jackson
(74) *Attorney, Agent, or Firm* — Donald R. Palladino

(57) ABSTRACT

The present invention provides a process for preparing di- and polyamines from the diphenylmethane series by converting aniline and formaldehyde in the absence of an acid catalyst to give aminal and water, removing the aqueous phase and further processing the organic aminal phase to give the di- and polyamines of the diphenylmethane series, in which use of a coalescence aid in the phase separation of the process product obtained in aminal reaction reduces the proportion of water and hence also of water-soluble impurities in the organic phase containing the aminal. The di- and polyamines of the diphenylmethane series obtained by acid-catalyzed rearrangement and workup after further processing of the aminal phase are outstanding suitably for preparation of the corresponding isocyanates.

7 Claims, No Drawings

PROCESS FOR THE PREPARATION OF DI- AND POLYAMINES FROM THE DIPHENYLMETHANE SERIES

CROSS-REFERENCE TO RELATED APPLICATIONS

This Application is a National Phase Application of PCT/EP2014/058044, filed Apr. 22, 2014, which claims priority to European Application No. 13165198.6, filed Apr. 24, 2013, each of which being incorporated herein by reference.

FIELD

The present invention relates to a process for the preparation of di- and polyamines of the diphenylmethane series by converting aniline and formaldehyde in the absence of an acid catalyst to give aminal and water, removing the aqueous phase and further processing the organic aminal phase to give the di- and polyamines of the diphenylmethane series, in which use of a coalescence auxiliary in the phase separation of the process product obtained in the aminal reaction reduces the fraction of water and hence also of water-soluble impurities in the organic aminal-comprising phase. The di- and polyamines of the diphenylmethane series obtained by acid-catalyzed rearrangement and work-up after further processing of the aminal phase are of outstanding suitability for the preparation of the corresponding isocyanates.

BACKGROUND

The preparation of di- and polyamines of the diphenylmethane series (MDA) from aniline and formaldehyde using acidic catalysts is generally known. In the context of the present invention, di- and polyamines of the diphenylmethane series are understood as meaning amines and mixtures of amines of the following type:

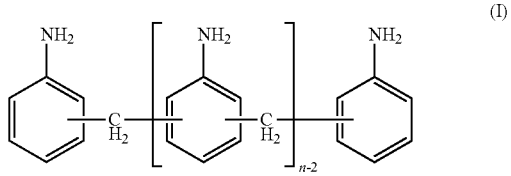

(I)

Here, n is a natural number ≥2. Hereinbelow, the compounds of this type in which n=2 are referred to as diamines of the diphenylmethane series or diaminodiphenylmethanes (subsequently MMDA). Compounds of this type in which n is >2 are referred to within the context of this invention as polyamines of the diphenylmethane series or polyphenylenepolymethylenepolyamines (subsequently PMDA). Mixtures of both types are referred to as di- and polyamines of the diphenylmethane series (subsequently MDA). The corresponding isocyanate, which can be derived formally by replacing all $NH_2$ groups by NCO groups from the compounds of formula (I) are accordingly referred to as diisocyanates of the diphenylmethane series (subsequently MMDI), polyisocyanates of the diphenylmethane series or polyphenylenepolymethylenepolyisocyanates (subsequently PMDI) or di- and polyisocyanates of the diphenylmethane series (subsequently MDI). Here, both in the case of the amine and also in the case of the isocyanate, the polymer (n>2) is generally always present in the mixture with the dimer (n=2), meaning that in practice only two compound types are relevant, the pure dimers (MMDA or MMDI) and the mixture of dimers and polymers (MDA or MDI).

Industrially, the di- and polyamine mixtures are converted predominantly by phosgenation to the corresponding di- and polyisocyanates of the diphenylmethane series. The continuous or partly discontinuous preparation of MDA is disclosed, e.g., in U.S. Pat. No. 5,286,760, EP-A-451442 and WO-A-99/40059. The preparation of MDA can take place by converting aniline and formaldehyde directly in the presence of an acidic catalyst or firstly, in the absence of an acidic catalyst, firstly converting aniline and formaldehyde to the so-called aminal, which is then rearranged in a subsequent process step under acid catalysis to the di- and polyisocyanates of the diphenylmethane series (so-called aminal process). The present invention deals with the aminal process. In both processes, the acid is neutralized after the rearrangement has taken place.

Commercially available formaldehyde generally comprises methanol, either as a result of production and/or intentionally added in order to increase the stability of the formaldehyde. In this connection, formaldehyde grades with (i) low contents of methanol (for customary industrial applications), (ii) medium contents of methanol (for in particular pharmaceutical applications) and (iii) high contents of methanol (for special applications) are available (cf. e.g. "J. Frederic Walker, Formaldehyde, Chapter 4, Commercial Formaldehyde Solutions, Third Edition, Robert E. Krieger Publishing Company, Huntington, N.Y., 1975"). According to the last-mentioned literature reference, the customary methanol content in formaldehyde solutions in case (i) is 0.3 to 1.5%, in case (ii) is 6.0 to 15% and in case (iii) is 32.5 to 43%. The specified limits and differences between the fields of application naturally do not apply in the strict sense. Thus, e.g. the publication "David F. Gould, Phenolic Resins, Reinhold Publishing Corporation, New York, London, 1959" discloses the use of a formaldehyde with an average methanol content (7 to 15%) in the preparation of phenol-formaldehyde resins. However, a technical-grade formaldehyde solution with a low methanol content (at most 2% by mass, generally 1 to 2% by mass) is usually used for the MDA preparation.

The work-up of the acidic reaction mixture obtained in the preparation is triggered according to the prior art by neutralization with a base. According to the prior art, the neutralization usually takes place at temperatures of for example 90° C. to 100° C. without the addition of further substances (H. J. Twitchett, Chem. Soc. Rev. 3(2), p. 223 (1974)). However, it can also take place at a different temperature level in order e.g. to increase the rate of the degradation of troublesome by-products. Hydroxides of the alkali metal and alkaline earth metal elements are suitable as bases. Preferably, aqueous NaOH is used.

After the neutralization, the organic phase is separated from the aqueous phase in a separation container. The organic phase comprising crude MDA which remains after the aqueous phase has been separated off is subjected to further work-up steps such as e.g. a washing with water (base washing) in order to wash residual salts from the crude MDA. Finally, the crude MDA purified in this way is freed from excess aniline, water and other substances present in the mixture (e.g. further solvents) by suitable methods such as e.g. distillation, extraction or crystallization. The work-up customary according to the prior art is disclosed for example in EP 1 652 835 A1, page 3, line 58 to page 4, line 13 and EP 2 103 595 A1, page 7, lines 21 to 37.

EP 1 616 890 A1 discloses a process in which aniline and formaldehyde are firstly converted in the absence of the acidic catalyst to aminal, and the aminal obtained in this way is then admixed with an acidic catalyst and converted further at temperatures of 20° C. to 100° C. and at water contents of the acidic reaction mixture obtained in this way of 0 to 20 percent by weight. In particular, after the condensation of formaldehyde and aniline to give the aminal, firstly the water is at least partly removed from the aminal, with a water content of 0 to 5 percent by weight being established in the aminal before the aminal is admixed with acidic catalyst. In this way, it is possible to prepare MDA with a degree of protonation of <15%, preferably 4 to 14%, particularly preferably 5 to 13%. The degree of protonation here for monobasic acidic catalysts (such as hydrochloric acid) is the term used to refer to the molar ratio of the amount of acidic catalyst used and the molar amount of amine functions present in the reaction mixture.

EP 1 813 598 A1 teaches (see in particular paragraphs [0037] to [0042]) that the water produced in the aminal reaction (water of reaction) and the water originating from the formalin is partly or completely combined with other waste water streams of the process and is further treated to remove organic constituents, such as e.g. aniline and MDA, such as e.g. a combination of extraction and distillation. The whereabouts of the feed material formalin is not described. Furthermore, EP 1 813 598 A1 (see paragraph [0043]) teaches that during the distillative aniline removal from the extracted waste water, the vapors can be condensed in multiple stages and, in so doing, a fraction comprising methanol and further low-boilers in high concentrations can advantageously be produced. Firstly, therefore, the methanol level in the process stages is advantageously reduced, and secondly this fraction can advantageously be used as a fuel substitute.

The quality of a process for the preparation of MDA is on the one hand defined by the content in the product of undesired byproducts of the reaction. On the other hand, the quality of a continuous process is defined by the fact that the overall process from start-up, normal production to shut-down of the process can be operated without technical production loss or problems which require intervention in the process, and that there are no resulting losses of feed materials, intermediate products or end product. Such problems can arise e.g. upon adjusting the water content in the aminal by phase separation of organic phase and aqueous phase. Problems of this type can be e.g. that it results in delays during phase separation, or that the phase separation is incomplete, or that a third phase (mulm or mulm layer) is formed. This third phase is a stable, sometimes voluminous interim phase which occurs between the aqueous phase and the organic phase and hinders the phase separation and, in extreme cases, even prevents it entirely. In the most unfavorable case for operational progress, the phase separation container or containers affected have to be completely emptied and cleaned. The content of the phase separation container or containers then has to be worked up, which is complex, or be disposed of, which is associated with considerable costs. In some circumstances, this can also lead to the continuous production having to be interrupted. If the formation of a mulm layer cannot be completely avoided, then this will ultimately end up in one of the two phases. If the mulm layer ends up in the organic phase, then, in the case of phase separation after the aminal reaction, this is less serious than if it ends up in the aqueous phase. This is because in the last-mentioned case, larger amounts of dispersely dissolved organic materials then end up in the aminal water with the mulm layer. Said losses can then arise during the disposal or further use of the aminal water.

EP 2 103 595 A1 deals with a procedure for the preparation of di- and polyamines of the diphenylmethane series in which aniline and formaldehyde are converted in the presence of an acidic catalyst. In connection with the phase separation after the neutralization of the crude product, it is disclosed that this phase separation can be assisted by adding water and/or aniline. Preferably, the reaction mixture diluted by adding water and/or aniline is separated into an organic phase and aqueous phase in separating flasks with plate sections, assisting the coalescence of the two phases, as internals (paragraphs [0043] and [0044]). Apart from the fact that the use of mechanical separation aids results in an additional expenditure on apparatus, completely satisfactory results cannot be achieved with plate sections if particularly high requirements are placed on the quality of a phase separation. This applies accordingly for the separation of the two phases after the aminal reaction for a process procedure for the preparation of di- and polyamines of the diphenylmethane series in which aniline and formaldehyde are reacted firstly in the absence of an acidic catalyst and the aminal formed is only rearranged in a subsequent process step with acid catalysis.

It would therefore be desirable to have available processing measures in order to be able to overcome these problems.

Although the described processes of the prior art succeed in preparing MDA with a high yield, no auxiliaries are described which, without additional expenditure on apparatus, could improve the separation of the organic phase from the aqueous aminal phase with the desirable efficacy in order to minimize the losses of feed materials and intermediate products in the reaction process and to ensure a seamless technical progress of the production process.

There was thus a need for a process for the preparation of di- and polyamines of the diphenylmethane series in which it is possible, by means of simple measures, to conduct an improved phase separation between organic phase and aqueous phase in the aminal stage. This would improve the cost-effectiveness of existing MDA processes.

SUMMARY

Taking into account that stated above, the present invention provides a process for the preparation of di- and polyamines of the diphenylmethane series in which
a) aniline and formaldehyde are converted in the absence of an acidic catalyst to a reaction mixture comprising aminal and water, where the formaldehyde to be used comprises at most 2.0% by mass, preferably 1.0% by mass to 2.0% by mass, of methanol;
b) water, which consists essentially of water of condensation of the aminal reaction and water from the feed material formaldehyde, is removed at least in part from the reaction mixture obtained in step a), giving an organic phase comprising the aminal;
c) the organic aminal-comprising phase obtained in step b) is converted in the presence of an acidic catalyst, giving a reaction mixture comprising di- and polyamines of the diphenylmethane series;
d) the reaction mixture comprising di- and polyamines of the diphenylmethane series obtained in step c) is neutralized and then subjected to a work-up involving washing and distillation;
wherein, for the purposes of assisting the separation, to be performed in step b), of the water from the reaction mixture obtained in step a), in step a) at least one auxiliary reagent from at least one of the groups (i) to (v) or at least one auxiliary reagent from exclusively group (vi) is added in the mass fractions stated in each case, the mass fractions referring to the total mass of all of the feed substances used in step a) including the mass of the auxiliary reagents added:

(i) 0.05% by mass to 3.0% by mass, preferably 0.1% by mass to 1.5% by mass, of aliphatic alcohols having 1 to 6 carbon atoms, (ii) 0.0001% by mass to 3.0% by mass, preferably 0.01% by mass to 1.5% by mass, of alkali metal halides, (iii) 0.0001% by mass to 0.030% by mass, preferably 0.001% by mass to 0.015% by mass, of alkali metal hydroxides, (iv) 0.0001% by mass to 1.0% by mass, preferably 0.001% by mass to 0.50% by mass, of carboxylic acids having 1 to 4 carbon atoms, (v) 0.0001% by mass to 1.0% by mass, preferably 0.001% by mass to 0.50% by mass, of salts of carboxylic acids having 1 to 4 carbon atoms, (vi) 0.1% by mass to 3.0% by mass, preferably 0.2% by mass to 1.5% by mass, of cycloaliphatic alcohols having 5 to 7 carbon atoms, where the mass fraction of the auxiliary reagent of group (vi) is selected such that this is greater than 0.5% by mass, based on the total mass of the aniline used in step a) and of the auxiliary reagent of group (vi).

The content of methanol, in the formaldehyde to be used in step a) is to be understood here as meaning the mass fraction of methanol in percent, based on the total mass of the formaldehyde in the form used (i.e. in the preferred case of the use of an aqueous formaldehyde solution including the mass of the water).

The invention also relates to a process for the preparation of di- and polyisocyanates of the diphenylmethane series in which di- and polyamines of the diphenylmethane series are prepared by the process according to the invention and are then converted with phosgene to the corresponding di- and polyisocyanates.

DETAILED DESCRIPTION

Embodiments of the invention are described in more detail below. Different embodiments can be combined with one another as desired provided the opposite does not clearly arise for the person skilled in the art from the context.

The condensation of aniline and formaldehyde in step a) can be carried out by a process according to the prior art apart from the requirement according to the invention of the addition of an auxiliary reagent (see in this respect the paragraph which follows). Here, preferably aniline and aqueous formaldehyde solution are condensed at a molar ratio of aniline to CH2O of 1.7:1 to 20:1, preferably 1.7:1 to 5.0:1 at a temperature of 20° C. to 100° C., preferably from 30° C. to 95° C., particularly preferably from 40° C. to 90° C., to give aminal and water. The conversion usually takes place at atmospheric pressure. Suitable aniline grades are described e.g. in EP 1 257 522 B1, EP 2 103 595 A1 and EP 1 813 598 B1. Preference is given to using technical grades of formalin (aqueous solution of formaldehyde) with 30% by mass to 50% by mass of formaldehyde in water. However, formaldehyde solutions with lower or higher concentrations or else the use of gaseous formaldehyde are also conceivable.

According to the invention, in step a) at least one auxiliary reagent is added as defined above. The auxiliary reagents can be added in a continuous, semicontinuous or batch process everywhere between inlet of the aminal reactor (i.e. the reactor in which step a) is carried out) to the inlet of the phase separation apparatus of step b). They can also be mixed beforehand with the feed streams aniline and/or formaldehyde. Moreover, it is possible to also firstly allow aniline and formaldehyde to react and only then to add the auxiliary reagent.

Particularly preferred auxiliary reagents are:
methanol and a methanol-containing process stream;
sodium chloride, potassium chloride and aqueous process streams of these salts;
sodium hydroxide and potassium hydroxide;
formic acid;
sodium formate and potassium formate;
cyclohexanol.

(In this connection, a "process stream" is understood as meaning a stream such as is produced as a result of the process at another point in the MDA production plant or in another production plant.) It is also possible to use mixtures of two or more of these auxiliary reagents provided it is ensured that cyclohexanol is not used in such mixtures: If solutions of auxiliary reagents are used (e.g. process streams or aqueous solutions of salt-like auxiliary reagents), then the respective concentration data which is to be observed according to the invention refers to the mass of the dissolved auxiliary reagent and not to the mass of the solution.

Very particularly preferably, methanol, a methanol-containing process stream, sodium chloride, a sodium chloride-containing aqueous process stream, an aqueous sodium hydroxide solution (sodium lye) or a combination of these auxiliary reagents or (exclusively) cyclohexanol is used. Extraordinarily very particular preference is given to the use of methanol, a methanol-containing process stream, a sodium chloride-containing process stream, an aqueous sodium hydroxide solution or a combination of these auxiliary reagents. Even more preferred is the use of methanol, a methanol-containing process stream, a sodium chloride-containing process stream or a combination of these auxiliary reagents.

If a combination of auxiliary reagents of different groups is used, then such a combination comprises according to the invention only the above-defined groups (i) to (v). This is because it has surprisingly been observed that combinations of (vi) cycloaliphatic alcohols with 5 to 7 carbon atoms, in particular cyclohexanol, with one or more of the other auxiliary reagents listed above from groups (i) to (v) lead to longer phase separation times than when dispensing with the addition of auxiliary reagents.

Based on the total mass of the feed materials of the aminal reaction (step a)), 0.05% by mass to 3.0% by mass, preferably 0.1% by mass to 1.5% by mass, of aliphatic alcohols having 1 to 6 carbon atoms and/or 0.0001% by mass to 3.0% by mass, preferably 0.01% by mass to 1.5% by mass, of alkali metal halides and/or 0.0001% by mass to 0.030% by mass, preferably 0.001% by mass to 0.015% by mass, of alkali metal hydroxides and/or 0.0001% by mass to 1.0% by mass, preferably 0.001% by mass to 0.50% by mass, of carboxylic acids having 1 to 4 carbon atoms or the salts of carboxylic acids having 1 to 4 carbon atoms or 0.1% by mass to 3.0% by mass, preferably 0.2% by mass to 1.5% by mass, of cycloaliphatic alcohols having 5 to 7 carbon atoms are added as auxiliary reagent. In the case of the cycloaliphatic alcohols having 5 to 7 carbon atoms, the restriction whereby the mass fraction of such an auxiliary reagent must be selected such that it is greater than 0.5% by mass, based on the total mass of the aniline used in step a) and the auxiliary reagent, must additionally be taken into account.

In the MDA process, preference is given to using inherently occurring chemical auxiliary reagents so as not to unnecessarily contaminate the process with foreign substances.

This procedure is also therefore not obvious to the person skilled in the art because the technical-grade formalin available on the market, which is usually used in the preparation of MDA, already comprises, depending on the preparation process, methanol in the order of magnitude from 1% by mass to 2% by mass, based on the total mass of the formalin. The person skilled in the art is in no way encouraged by the prior art to admix such formalin of technical grade with additional methanol (or one of the other specified auxiliary reagents).

In step b) the phase separation of organic aminal phase and aqueous phase takes place at a temperature of 20° C. to 100° C., preferably from 30° C. to 95° C., particularly preferably from 40° C. to 90° C., preferably at ambient pressure. As a result of the addition according to the invention of an auxiliary reagent, the organic fraction in the aqueous phase separated after the aminal reaction (step a)) (so-called "aminal water") is minimized (clarification of the residual cloudiness) and thus the phase separation is facilitated.

The rearrangement of the aminal in step c) takes place in the presence of an acidic catalyst, usually a strong mineral acid such as hydrochloric acid. Preference is given to the use of mineral acid in a molar ratio mineral acid:aniline of 0.001:1 to 0.9:1, preferably 0.05:1 to 0.5:1. It is naturally also possible to use solid, acidic catalysts as described in the literature. In this connection, formaldehyde can be added to a mixture of aniline and acidic catalyst and the reaction solution can be fully reacted by stepwise heating. Alternatively, aniline and formaldehyde can also firstly preact and then be admixed, with or without prior water removal, with the acidic catalyst or a mixture of further aniline and acidic catalyst, after which the reaction solution is fully reacted by stepwise heating. This reaction can be carried out continuously or discontinuously with one of the numerous processes described in the literature (e.g. in EP 1 616 890 A1 or EP 1 270 544 A1).

In step d) the reaction mixture comprising the di- and polyamines of the diphenylmethane series is firstly neutralized optionally with the addition of water and/or aniline (step d.1)). The neutralization preferably takes place at a temperature of 90° C. to 100° C. without the addition of further substances. However, it can also take place at a different temperature level in order to increase the rate of e.g. the degradation of troublesome byproducts. Suitable bases are preferably the hydroxides of the alkali metal and alkaline earth metal elements. Preference is given to using sodium hydroxide solution. The base used for the neutralization is preferably used in an amount of more than 100%, particularly preferably 105% to 120%, of the amount required stoichiometrically for the neutralization of the acidic catalyst used (see EP 1 652 835 A1). The two-phase mixture obtained in this way is then separated into an organic phase comprising di- and polyamines of the diphenylmethane series and an aqueous phase. This can be assisted by the addition of aniline and/or water. If the phase separation is assisted by adding aniline and/or water, then their addition preferably already takes place with intensive mixing in the neutralization. In this connection, the mixing can take place in mixing sections with static mixers, in stirred tanks or stirred-tank cascades or else in a combination of mixing sections and stirred tanks. The neutralized reaction mixture, optionally diluted by adding aniline and/or water, is then preferably fed to an apparatus which, on account of its configuration and/or internals, is particularly suitable for separation into an organic phase comprising MDA and an aqueous phase, preferably phase separation or extraction devices corresponding to the prior art, as are described for example in Mass-Transfer Operations, 3rd Edition, 1980, McGraw-Hill Book Co, p. 477 to 541, or Ullmann's Encyclopedia of Industrial Chemistry (Vol. 21, Liquid-Liquid Extraction, E. Miller et al., pages 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", Published Online: Jun. 15, 2007, pages 22-23) (mixer-settler cascade or settling container). The residence times and residence time distributions in the phase separation apparatuses of the neutralization and washing can be improved by technical internals in order to bring about improved separation effects.

The organic phase obtained in this way is then subjected to a washing (step d.2)). The washing liquid used is preferably water. The wash water is then separated by means of phase separation. In this way, the salt content of the organic phase is reduced. A suitable preferred process is described for example in DE-A-2549890, in particular on page 3. The phase separation can be improved by adding a small amount of sodium hydroxide solution to the wash water in step d.2). The amount of sodium hydroxide solution can be readily determined by a person skilled in the art. The organic phase obtained in step d.2) preferably has a composition, based on the total mass of this organic phase, of 5.0% by mass to 15% by mass of water and, depending on use ratios of aniline and formaldehyde, 5.0% by mass to 90% by mass, preferably 5.0% by mass to 40% by mass, of aniline and 5.0% by mass to 90% by mass, preferably 50% by mass to 90% by mass, of di- and polyamines of the diphenylmethane series. After emerging from the phase separation in step d.2), the organic phase comprising di- and polyamines of the diphenylmethane series usually has a temperature of 80° C. to 150° C.

Then, water and aniline are separated off by distillation, as known in the prior art, from the resulting neutralized and washed organic phase comprising di- and polyamines of the diphenylmethane series (step d.3)). This takes place preferably as described in EP 1 813 597 B1, in particular in paragraphs [0014] to [0043].

The thus obtained di- and polyamines of the diphenylmethane series can be converted by the known methods with phosgene to the corresponding di- and polyisocyanates of the diphenylmethane series. In this connection, the phosgenation can be carried out by one of the processes known from the prior art (e.g. DE-A-844 896 or DE-A-198 17 691).

If an auxiliary reagent is added in the aminal reaction (step a)) in order to assist the removal of organic substances (essentially aminal) from the aminal water which is then to be performed, i.e. if the organic substance content in the aminal water is reduced and the thus obtained organic substances are further processed according to the invention in steps c) and d), then the following advantages arise inter alia:

1) The preparation costs of the process are improved because the losses of feed materials and intermediates via the aqueous phase are minimized.
2) The reduced loading of the aqueous phase with organic substances leads to a lower treatment cost in the waste water processing (energy costs are saved because less steam is required for stripping off organic substances from the MDA waste water).

3) The use of overdimensioned phase separation apparatuses which permit a phase separation of the aminal reaction mixture over a very long residence time can be dispensed with.
4) Reduction in impurities and deposits in the reaction apparatuses and in the stripping of the waste water.
5) More efficient use of the acidic catalyst in the rearrangement reaction of the aminal.

EXAMPLES

Content data in % are percentages by mass based on the total mass of the particular substance.

Example 1 (Comparison)

A multi-neck round-bottomed flask was charged with 279 g of pure aniline and, at 80° C. with stirring, 134 g of a 32% strength aqueous technical-grade formaldehyde solution, which had a methanol content of 1.2% by mass, were added dropwise over the course of 20 min. When the addition of formaldehyde was complete, the mixture was after-stirred for a further 5 min and a phase separation was performed at 80° C. 89 seconds after switching off the stirrer the onset of phase separation became evident from the appearance of a foam-like consistency; after 160 seconds, the separation of the organic and aqueous phase was complete (see also table 1).

Example 2 (According to the Invention)

A multi-neck round-bottomed flask was charged with 279 g of pure aniline and, at 80° C. with stirring, 134 g of a 32% strength aqueous technical-grade formaldehyde solution, which had a starting methanol content of 1.2% by mass and to which, prior to use as starting material, an additional 1.0% by mass of methanol, based on the total mass of the aqueous formaldehyde used, had been admixed as auxiliary, were added dropwise over the course of 20 min. After completion of the addition of formaldehyde, the mixture was after-stirred for a further 5 min and a phase separation was performed at 80° C. 20 seconds after switching off the stirrer, the onset of phase separation became evident from the appearance of a foam-like consistency; after 36 seconds, the separation of the organic and aqueous phase was complete (see also table 1).

Examples 3-8 and 10-12 (According to the Invention), Example 9 (Comparison)

A multi-neck round-bottomed flask was charged with 279 g of pure aniline and, at 80° C. with stirring, 134 g of a 32% strength aqueous technical-grade formaldehyde solution, which had a starting methanol content of 1.2% by mass and to which, prior to use as starting material, additional auxiliary reagents had been admixed, were added dropwise over the course of 20 min. Following completion of the addition of formaldehyde, the mixture was after-stirred for a further 5 min and after switching off the stirrer at 80° C. a phase separation was performed. Table 1 summarizes the auxiliaries and the observed separation times of the phase separation.

TABLE 1

| Example | Auxiliary reagent | Fraction of added auxiliary reagent in % by mass, based on the total mass of the reaction mixture | Foam formation in seconds | Complete separation of the phases in seconds |
| --- | --- | --- | --- | --- |
| 1 (comparison) | Without | — | 89 | 160 |
| 2 (according to the invention) | Methanol | 0.32 [a] | 20 | 36 |
| 3 (according to the invention) | NaCl | 0.0032 | 21 | 55 |
| 4 (according to the invention) | NaCl | 0.032 | 21 | 42 |
| 5 (according to the invention) | NaCl | 0.16 | 21 | 43 |
| 6 (according to the invention) | NaCl | 0.32 | 24 | 54 |
| 7 (according to the invention) | NaOH | 0.0016 | 22 | 43 |
| 8 (according to the invention) | NaOH | 0.0065 | 20 | 47 |
| 9 (comparison) | NaOH | 0.032 | 120 | 210 |
| 10 (according to the invention) | Formic acid | 0.0016 | 21 | 35 |
| 11 (according to the invention) | Formic acid | 0.0065 | 21 | 50 |
| 12 (according to the invention) | Formic acid | 0.032 | 22 | 38 |

[a] Only the deliberately added fraction of methanol is given, without the methanol already present in technical-grade formaldehyde.

The table shows that the presence of auxiliary reagents in the concentrations according to the invention in the aminal reaction (step a)) improves the subsequent phase separation (step b)). Surprisingly, this is also applicable for methanol, which is indeed already present in amounts of 1 to 2% by mass in the aqueous technical-grade formaldehyde solution. Example 9 with the auxiliary reagent NaOH shows that the auxiliary reagents only have a positive effect within a certain concentration range.

Examples 13-17 (Comparison)

A multi-neck round-bottomed flask was charged with 279 g of pure aniline, to which cycloaliphatic amines were admixed with stirring. Then, at 80° C. and with stirring, 134 g of a 32% strength aqueous technical-grade formaldehyde solution, which had a methanol content of 1.2% by mass, were added dropwise over the course of 20 min. After the addition of formaldehyde was complete, the mixture was after-stirred for a further 5 min and, after switching off the stirrer at 80° C., a phase separation was performed. Table 2 summarizes the additives and the observed separation times of the phase separation.

Examples 18-21 (According to the Invention)

A multi-neck round-bottomed flask was charged with 279 g of pure aniline, to which different amounts of cyclohexanol were admixed with stirring. Then, at 80° C. and with stirring, 134 g of a 32% strength aqueous technical-grade formaldehyde solution, which had a methanol content of 1.2% by mass, were added dropwise over the course of 20 min. After the addition of formaldehyde was complete, the mixture was after-stirred for a further 5 min and, after switching off the stirrer at 80° C., a phase separation was performed. The results can likewise be found in table 2.

TABLE 2

| Example | Auxiliary reagent | Fraction of added auxiliary reagent in % by mass, based on the total mass of the reaction mixture | Foam formation in seconds | Complete separation of the phases in seconds |
|---|---|---|---|---|
| 1 (comparison) | Without | — | 89 | 160 |
| 13 (comparison) | Cyclo-hexyl-amine | 0.0068 | 110 | No complete separation |
| 14 (comparison) | Cyclo-hexyl-amine | 0.068 | 330 | No complete separation |
| 15 (comparison) | Cyclo-hexyl-amine | 0.135 | 600 | No complete separation |
| 16 (comparison) | Dicyclo-hexyl-amine | 0.068 | No phase separation | No phase separation |
| 17 (comparison) | Dicyclo-hexyl-amine | 2 | 1800 | No complete separation |
| 18 (according to the invention) | Cyclo-hexanol | 0.0068 | 19 | 49 |
| 19 (according to the invention) | Cyclo-hexanol | 0.068 | 17 | 54 |
| 20 (according to the invention) | Cyclo-hexanol | 0.68 | 19 | 47 |
| 21 (according to the invention) | Cyclo-hexanol | 2 | 20 | 58 |

The table shows that the presence of cycloaliphatic amines in the aminal reaction interferes with the subsequent phase separation. Surprisingly, the addition of cyclohexanol within a wide concentration range significantly improves the phase separation.

Example 22 (Comparison, Auxiliary Mixture with Cyclohexanol)

A multi-neck round-bottomed flask was charged with 279 g of pure aniline, to which 2.8 g of cyclohexanol were admixed with stirring. Then, at 80° C. and with stirring, 134 g of a 32% strength aqueous technical-grade formaldehyde solution, which had a methanol content of 1.2% by mass and to which additionally 0.7 g of NaCl, 0.07 g of NaOH and 1.3 g of methanol had been added, were added dropwise over the course of 20 min. When the addition of formaldehyde was complete, the mixture was after-stirred for a further 5 min and, after switching off the stirrer at 80° C., a phase separation was performed. The result of this experiment can be found in table 3.

TABLE 3

| Example 22 | Auxiliary reagents | Fraction of added auxiliary reagent in % by mass, based on the total mass of the reaction mixture | Foam formation in seconds | Complete separation of the phases in seconds |
|---|---|---|---|---|
| Auxiliary mixture with cyclohexanol | Methanol | 0.32 | 150 | 210 |
| | NaCl | 0.16 | | |
| | NaOH | 0.016 | | |
| | Cyclo-hexanol | 0.68 | | |

Example 23 (Comparison, Operational Test in a Production Plant)

In a continuous reaction process (step a)), 24.4 t/h of feed aniline (comprising 90% by mass of aniline) and 6.1 t/h of 50% strength formaldehyde solution, which comprised 1.0% by mass of methanol, were mixed and converted continuously to the aminal at 95° C. in a stirred reaction vessel. The subsequent phase separation (step b)) in a phase separation apparatus proved difficult since the phase separation layer was difficult to see on account of clouding in the aqueous phase and the appearance of a mulm layer. On account of an emerging emulsion, the plant had to be shut down and the phase separation container had to be emptied before restarting the aminal reaction.

Example 24 (According to the Invention, Operational Test in a Production Plant)

In a continuous reaction process (step a)), 24.4 t/h of feed aniline (comprising 90% by mass of aniline) and 6.1 t/h of 50% strength formaldehyde solution, which comprised 1.0% by mass of methanol, were mixed and converted continuously to the aminal at 95° C. in a stirred reaction vessel. Additionally, in a continuous procedure, 200 l/h of a salt-containing aqueous process stream which comprised 8% by mass of NaCl and 0.5% by mass of NaOH and had a conductivity of 145 mS were added to the reactor. The reaction mixture leaving the reaction vessel was admixed continuously with 60 l/h of a methanol-containing process stream (45% by mass of methanol in water) and passed to a phase separation apparatus (step b)). The phase separation took place without problems since a highly visible phase separation layer was formed. The process could be performed stably over a long production phase.

Following phase separation to remove the aqueous phase, the organic phase was admixed with 31% strength aqueous hydrochloric acid (degree of protonation 10%, i.e. 0.1 mol of HCl was added per mole of amino groups) and reacted at 50° C. to 150° C. in a reactor cascade (step c)). Following complete reaction, the resulting reaction mixture was admixed with 32% strength sodium hydroxide solution in the molar ratio of 1.1:1 sodium hydroxide solution to HCl and reacted in a neutralization stirred container (step d.1)). The temperature was 115° C. The absolute pressure was 1.4 bar. The neutralized base mixture was then separated in a neutralization separator into an aqueous, lower phase, which was passed to a waste water collecting container, and into an organic phase. The organic, upper phase was passed to the washing (step d.2)). In a stirred washing container, the alkaline MDA was washed with condensate. After separating off the wash water in a wash water separator, the crude MDA obtained in this way was freed from water and aniline in step d.3)) by distillation, with 17 t/h of MDA being obtained as bottom product.

The invention claimed is:

1. A process for the preparation of di- and polyamines of the diphenylmethane series, comprising:
   a) converting aniline and formaldehyde in the absence of an acidic catalyst to a reaction mixture comprising aminal and water, where the formaldehyde to be used comprises at most 2.0% by mass of methanol;
   b) removing water at least in part from the reaction mixture obtained in step a), giving an organic phase comprising the aminal;
   c) converting the organic aminal-comprising phase obtained in step b), in the presence of an acidic catalyst, to a reaction mixture comprising di- and polyamines of the diphenylmethane series; and
   d) neutralizing the reaction mixture comprising di- and polyamines of the diphenylmethane series obtained in step c) and then subjecting the reaction mixture to a work-up comprising washing and distillation;
wherein
in step a) at least one auxiliary reagent from at least one of the groups (i) to (v) or at least one auxiliary reagent from exclusively group (vi) is added in the mass fractions stated in each case, the mass fractions referring to the total mass of all of the feed substances used in step a) including the mass of the auxiliary reagents added:
(i) 0.05% by mass to 3.0% by mass of aliphatic alcohols having 1 to 6 carbon atoms,
(ii) 0.0001% by mass to 3.0% by mass of alkali metal halides,
(iii) 0.0001% by mass to 0.030% by mass of alkali metal hydroxides,
(iv) 0.0001% by mass to 1.0% by mass of carboxylic acids having 1 to 4 carbon atoms,
(v) 0.0001% by mass to 1.0% by mass of salts of carboxylic acids having 1 to 4 carbon atoms,
(vi) 0.1% by mass to 3.0% by mass of cycloaliphatic alcohols having 5 to 7 carbon atoms, where the mass fraction of the auxiliary reagent of group (vi) is selected such that this is greater than 0.5% by mass, based on the total mass of the aniline used in step a) and of the auxiliary reagent of group (vi).

2. The process of claim 1, in which
the auxiliary reagent of group (i) is selected from the group consisting of methanol and a methanol-containing process stream,
the auxiliary reagent of group (ii) is selected from the group consisting of sodium chloride, potassium chloride and aqueous process streams of these salts,
the auxiliary reagent of group (iii) is selected from the group consisting of sodium hydroxide and potassium hydroxide,
the auxiliary reagent of group (iv) is formic acid,
the auxiliary reagent of group (v) is selected from the group consisting of sodium formate and potassium formate,
the auxiliary reagent of group (vi) is cyclohexanol.

3. The process of claim 1, in which only auxiliary reagents of groups (i), (ii), (iii) and (vi) are used and in which
the auxiliary reagent of group (i) is selected from the group consisting of methanol and a methanol-containing process stream,
the auxiliary reagent of group (ii) is selected from the group consisting of sodium chloride and a sodium chloride-containing aqueous process stream,
the auxiliary reagent of group (iii) is an aqueous sodium hydroxide solution,
the auxiliary reagent of group (vi) is cyclohexanol.

4. The process of claim 1, in which only auxiliary reagents of the groups (i), (ii) and (iii) are used, and in which
the auxiliary reagent of group (i) is selected from the group consisting of methanol and a methanol-containing process stream,
the auxiliary reagent of group (ii) is selected from the group consisting of sodium chloride and a sodium chloride-containing aqueous process stream,
the auxiliary reagent of group (iii) is an aqueous sodium hydroxide solution.

5. The process of claim 1, comprising
introducing the at least one auxiliary reagent separately from the starting materials aniline and formaldehyde' to the conversion of step a)
or
adding the at least one auxiliary reagent to at least one of the starting materials aniline and formaldehyde of step a) before they are mixed
or
adding the at least one auxiliary reagent after mixing aniline and formaldehyde.

6. A process for the preparation of di- and polyisocyanates of the diphenylmethane series comprising phosgenation of di- and polyamines of the diphenylmethane series prepared by the process of claim 1.

7. The process of claim 1, in which only auxiliary reagents of groups (ii), (iii) and (vi) are used.

* * * * *